US006872071B1

(12) United States Patent
Durst (10) Patent No.: US 6,872,071 B1
(45) Date of Patent: Mar. 29, 2005

(54) DEVICE FOR ADJUSTING THE OXIDATION AGENT/FUEL MIXTURE IN THE FEEDING PIPE OF A BURNER

(75) Inventor: Franz Durst, Langensendelbach (DE)

(73) Assignee: Gesellschaft zur Verwertung der Gasartenerkennungstechnik in Brennersystemen (GVGB), Erlangen (DE)

( * ) Notice: Subject to any disclaimer, the term of this patent is extended or adjusted under 35 U.S.C. 154(b) by 0 days.

(21) Appl. No.: 09/959,436

(22) PCT Filed: Apr. 26, 2000

(86) PCT No.: PCT/EP00/03761

§ 371 (c)(1),
(2), (4) Date: Oct. 25, 2001

(87) PCT Pub. No.: WO00/65280

PCT Pub. Date: Nov. 2, 2000

(30) Foreign Application Priority Data

Apr. 26, 1999 (DE) .......................... 199 18 901

(51) Int. Cl.[7] ................................ F23N 5/00
(52) U.S. Cl. .......................... 431/90; 137/92
(58) Field of Search ............... 431/12, 89, 90; 132/4, 92, 101.31; 73/54.04, 54.09, 54.01; 374/37; 436/143

(56) References Cited

U.S. PATENT DOCUMENTS

| 4,384,792 | A | * | 5/1983 | Sommers et al. ............ 374/36 |
| 5,167,450 | A | * | 12/1992 | Nukui et al. ................ 374/31 |
| 5,311,447 | A | | 5/1994 | Bonne |
| 5,401,162 | A | * | 3/1995 | Bonne ........................ 431/89 |
| 5,486,107 | A | * | 1/1996 | Bonne ........................ 431/89 |
| 5,635,626 | A | * | 6/1997 | Hammond et al. ......... 73/23.2 |
| 6,178,811 | B1 | * | 1/2001 | Bonne et al. ............. 73/54.04 |
| 2004/0106078 | A1 | * | 6/2004 | Goebel ...................... 431/12 |

FOREIGN PATENT DOCUMENTS

| DE | 29 28 739 C2 | 6/1980 |
| EP | 0 628 815 | 12/1994 |
| GB | 1 571 906 | 7/1980 |
| GB | 2 296 091 | 6/1996 |

OTHER PUBLICATIONS

Linnemann, R. et al., A Self–Priming and Bubble–Tolerant Piezoelectric Silicon Micropump for Liquids and Gases, Fraunhofer–Institute for Solid State Technology, Munich Germany, Micro Electro Mechanical Systems MEMS, Jan 25–29, 1999.

* cited by examiner

*Primary Examiner*—Sara Clarke
(74) *Attorney, Agent, or Firm*—Arnold International; Bruce Y. Arnold (57) ABSTRACT

The invention relates to a device for adjusting the mixture of oxidation agent/fuel in the feeding pipe (22) of a burner. Said device comprises means (32, 12) for changing the composition of the oxidation agent/fuel mixture and a measuring instrument (2) for detecting the condition of the oxidation agent/fuel mixture and a circuit (28) for controlling said means (32, 12) for changing the composition on the basis of the condition detected by the measuring instrument. The invention is characterized in that the measuring instrument detects the condition of at least one partial mixture of the oxidation agent/fuel mixture via the viscosity or a function therefore before the combustion and that it is located upstream, in terms of the direction of flow, of the means (32, 12) for changing the composition. The invention is also characterized in that the measuring instrument controls the composition in accordance with a function of the detected viscosity by means of the circuit for controlling the means (32, 12) or that it is located downstream of the means (32, 12) for changing the composition and that it controls the composition of the oxidation agent/fuel mixture by means of the circuit for controlling the means (32, 12).

6 Claims, 5 Drawing Sheets

DEVICE FOR ADJUSTING THE OXIDATION AGENT/FUEL MIXTURE IN THE FEEDING PIPE OF A BURNER

The invention relates to a device for adjusting the oxidation agent/fuel mixture in the feeding pipe of a burner with a means for changing the composition of the oxidation agent/fuel mixture and a measurement device for detecting the condition of the oxidation agent/fuel mixture when burned and a circuit for controlling the means for changing the composition depending on the condition which has been detected by the measurement device.

In heating technology there has long been the problem that the combustion behavior of gas burners depends largely on the quality of the gas which is present locally. The quality is characterized by the upper Wobbe index $W_0$ which, according to Buderus Heiztechnik GmbH: *Handbuch der Heizungstechnik* [*Handbook for Heating Technology*], Beuth Verlag GmbH, Berlin, Vienna, Zurich, 33rd Edition, 1994, for Type L natural gas is in the range from 10.5 to 13 KWh/m$^3$ and for Type H natural gas is in the range from 12.0 to 15.7 KWh/m$^3$. Efforts have been made to build burners which can be operated not only with gases of one group at a time, but with gases of both groups. High-caloric gases have a high, low caloric gases have a low oxidation agent demand. When oxidation agents are mentioned here below, generally air is meant, but especially oxygen-enriched air or entirely different oxidation agents can be used.

In conventional burner controls the supply of the quantity of gas is not matched to the gas quality; this leads to a shift of the air excess number and thus generally to an unwanted change of the combustion process. For extremely high-caloric gases this can however lead to there being too little oxidation agent in the combustible gas mixture and thus increased production of pollutants, conversely the flame for very low caloric gases can be completely blown out by an overly large amount of oxidation agent. This in turn leads to limitations of the operating range of the burner because the legally prescribed emission threshold values can be exceeded due to the low efficiency and simple extinguishment of the flame. It should therefore be possible to adjust a burner such that all possible gas qualities or quality classes can be safely burned with low emissions.

The problem is also the same in combustion of gaseous fuels, especially gases of the first to the fourth gas family, alkanes, alkenes, alkines and gas mixtures which contain methane, higher hydrocarbons, hydrogen, nitrogen, carbon monoxide, carbon dioxide and air to a large extent. Here the fuel or the amount of air or oxidation agent should be matched to the type of fuel.

The same applies to liquid or multi phase fuels. Liquid fuels include for example propellants, liquified combustible gases and oils, in particular, diesel fuel, heating oils and rapeseed oils. Multi phase fuels include for example solid fuel particles which are transported for example in the gaseous phase, boiling fuels or liquid fuels which contain inert gases.

More and more a technology is being used with which the quality of the fuel or generally the condition of the fuel is recognized and the air ratio is controlled accordingly. This of course does not preclude the possibility of adjusting the fuel quality by also using additives according to a constant calorific value.

In general, the composition for the burner is controlled such that the burner works at least in the vicinity of an optimum operating point. In this way the operating range of a burner is widened, in any case complex processes for exact control of the required air or amount of oxidation agent which are then based mainly on measurements in burner operation cannot be technically implemented if the cost for the burner is to be kept as low as possible.

Some concepts for implementing combustion which is independent of the combustible gas composition are indicated below. One possibility is based on the measurement of the ionization flow during combustion. In this respect reference is made to the article of M. Hears, R. Marker, Dr. R. Naumann, H. Nolte: "*Optimierung von Verbrennungsprozessen mittels eines Ionisations-Flammen-Managements*" [Optimization of Combustion Processes by Means of Ionization Flame Management], Gas Wärme International, 47 (1998), Number 2; and "*Signale aus der Flamme, Luftzahlerkennung aus dem Ionisationstrom: Neue Möglichkeiten für die Kesseltechnik*" [Signals from the Flame, Air Ratio Detection from the Ionization Flow: New Potential for Boiler Engineering], Ruhrgas Forum, Number 7, Essen, 1998.

The ionization electrodes are a component of the safety chain of the burner which turns off the gas supply when the flame is extinguished. The measurement process used is based on the physical effect that the molecules of the gas-air mixture and its reaction products at the high temperatures in the flame split into electrically conductive ions. If a voltage is applied between the burner and ionization electrode, an electrical current flows as long as the flame burns.

In addition to detecting the flame on/off condition, the ionization flow however contains further information about the combustion condition, among others about the combustion temperature and thus indirectly about the air ratio. Calibration produces a reference with respect to stoichiometric operation which is characterized by the maximum value of the ionization flow. The operating point which is leaner than stoichiometric is established relative to this reference value and forms the basis of control.

Another possibility for achieving improved combustion conditions is based on measurement of the concentration of oxidation agent in the exhaust gas, as is done for example in automotive engineering as well. In doing so, so-called lambda probes are used, as are described for example in the product information of the company Gasmodul (Honeywell Co.): "Boiler control MCBA 1400 and GMS-10 $O_2$ sensor". Lambda probes consist essentially of two electrodes which are connected to one another by a solid electrolyte. This solid electrolyte is able to guide ions of oxygen which is used here as the oxidation agent. When an electrical DC voltage is applied a electrochemical pumping action is formed, as a result of which oxygen ions are routed through the solid electrolyte. Selective pumping of the oxygen ions results in a concentration gradient which produces a Nernst voltage. The time interval which is needed for the voltage difference to reach a set point is used as a measure for the partial oxidation agent pressure of the environment.

Another process for controlling a gas burner with consideration of the gas composition is the use of fiber optic measurement engineering. The radiation which is emitted by the flame and which is dependent on the mixture composition is detected by an optical probe and is routed to a photo multiplier via an optical fiber. The signal of the photo multiplier can be used then as the controlled variable for gas quantity supply. One such control system is described for example in the article "Neuss Regelsystem für Vormischbrenner, Lichtleiter-Meßtechnik erfaßt Flammensignale," [New control system for premixing burners, fiber optic measurement technology detects flame signals], Ruhrgas Forum, Edition 4, Essen, December 1992.

For measurement and control of the amount of heat supplied, there is another process as claimed in German patent disclosure document DE 43 36 174 A1 in which, by measurement of the volumetric flow of the gas, the pressure, the temperature, the density and the speed of sound under normal conditions and the speed of sound under operating conditions, conclusions can be drawn regarding the amount of heat transported in the fuel.

According to DE 29 28 739 a partial flow of the combustible gas is branched off and reacted in a calorimeter vessel. The combustible gas composition can be determined from the amount of heat which is released by means of a functional relationship. The measured value which has been delivered in this way can be used as a signal for control processes in order to keep the Wobbe index of the gas flow constant by supplying a gas, or to feasibly change the amount of gas flow. These processes are used by gas suppliers for checking or controlling the gas quality or in larger industrial plants for burner adjustment.

In principle, all these processes contain the measurement of different physical quantities via a measurement device and open-loop and closed-loop control via a circuit with which a means for changing the composition controls the mixing according to the signals delivered by the measurement device. Here, control is carried out according to the object of matching the combustion process to fluctuations of the fuel quality.

To date, only those processes for burners, in particularly household burners, which determine the measured values obtained via ionization flow measurement or a lambda probe for control during or after combustion have technically predominated. Accordingly, it is not possible to react to the change of gas quality before the start of combustion.

Other decisive technical disadvantages with respect to the lambda probe are short service life, with respect to ionization flow measurement of the thermal loads of the burner system which arise with the result of high development of pollutants as the stoichiometry point is approached.

Furthermore, in ionization flow measurement, faulty measurements occur because in principle re-calibration would be necessary for each new output adjustment. Continuous modulation is therefore technically extremely difficult to achieve. For example, there is a limit to operation with a limited number of output stages.

The aforementioned calorimetric determination of the gas means a certain energy loss. For reasons of cost, calorimetric determination of the gas composition for heating plants cannot be recommended.

The object of the invention is to devise an improved device for adjusting the oxidation agent/fuel ratio in the feeding pipe of a burner of the initially mentioned type, with costs which remain within reasonable limits.

The object is achieved using a device in which the measurement device detects the condition of at least one partial mixture of the oxidation agent/fuel mixture via the viscosity (or a function of the viscosity) before combustion. In the aforementioned device, this measurement instrument is located upstream, in terms of the direction of flow, of the means for changing the composition and controls the composition of the oxidation agent/fuel mixture according to a function of the detected viscosity using the circuit for controlling the means. Or, in the aforementioned device, this measurement device is located downstream of the means for changing the composition and using the circuit for controlling the means controls the composition of the oxidation agent/fuel mixture.

That the object is advantageously achieved with one such device is first of all unexpected. It would have been expected that a person skilled in the art would have optimized the known processes by means of ionization flow measurements or a lambda probe by special construction or determination of other parameters for improving control. But here a completely different approach is taken, especially by measuring the composition upstream of the burner. The sole process known in this respect would have been calorimetric determination of the calorific value which, however, entails a certain energy loss and has not been used to date for burner control.

Furthermore, the viscosity of at least one partial mixture is determined the first time, a physical quantity which to date had not been considered in burner control, possibly because the relationship between viscosity and calorific value explained in greater detail below is little known among specialists.

After completion of the invention, it was ascertained that, in addition to achieving the aforementioned object, the invention also offers other advantages. Thus the device as claimed in the invention can be used even before ignition of the flame for matching the burner to the changed properties of the fuel. In this way the ignition process can be facilitated. Ignition difficulties which occur especially for low-caloric gases can usually be eliminated only with complex measures for optimization of burner configurations. Furthermore, the starting emissions can hereby be purposefully controlled to a low level.

Furthermore, continuous operation is possible since the amount of air itself is corrected in a suitable manner when the fuel supply is choked. A burner which is operated with one such device need therefore not be turned on and off for heating at different stages. That is, ignition process which in conventional combustion contribute significantly to the exhaust emission of a burner can be avoided; this likewise contributes to improved environmental protection.

But overall it should be emphasized that it becomes possible using this technology to burn the fuel more completely; this also has a beneficial effect in the operation costs of a burner. Maintenance cycles, for example—to remove fuel residues, can be reduced due to the resulting, almost complete, combustion.

Based on the process which is completely newly used in the device, the device can even be used for burner control for the most varied types of fuel. Furthermore, the device, depending on the arrangement of the measurement device, can be used either upstream or downstream of the means for changing the composition, with open-loop or closed-loop control. Open-loop control is preferred because it has been found that the Wobbe index can be determined much better when the viscosity is detected in a pure fuel mixture without oxidation agent being supplied.

To explain the invention with respect to physical circumstances, reference is made to DE 29 28 739, which published the finding that the fuel properties of natural gases of varied origin and composition can be determined with great accuracy as a function of the dynamic viscosity of fluids. This finding has not been exploited to date in the control of burners. In the publication this process is recommended solely for devising a reasonable measure for billing the amounts of fuel delivered. The process however has not become popular there; essentially calorimetric methods continue to be used for billing.

The basis for determining the calorific value or the Wobbe index from viscosity will be briefly explained as follows:

The upper Wobbe index $W_0$ at the prevailing pressure and temperature condition of the combustible gas is recognizably an important fuel quality value of gaseous fuels and is defined by the expression:

$$W_O = H_O/(\rho/\rho_{L,n})^{0.5} \quad (1)$$

where $H_O$ is the operating useful output, $\rho$ is the density of the combustible gas and $\rho_{L,n}$ is the standard density (273.15 K and 1013.25 hPa) of air. The lower Wobbe index $W_u$ is defined analogously, and instead of the useful output $H_O$ the calorific value $H_u$ must be used.

The viscosity can be determined by way of example when under the assumption of laminar gas flow in a capillary or a tube the following physical regularity is used as the basis (Hagen-Poiseuile law):

$$\eta = (\Delta p \pi R^4)/(8LV) \quad (2)$$

Here:
$\eta$ dynamic gas viscosity
$\Delta p$ pressure difference between the inlet and outlet or the two pressure measurement sites,
R radius of the capillary
L length of the capillary and
V volumetric flow of the fuel gas.

As an alternative to equation (2) which is valid in the laminar region, the use of a somewhat more complex relationship which is dependent on the pipe rank for incompletely formed turbulence, i.e., in the transition region between the laminar and completely turbulent flow, would be possible. Another alternative consists in using non-circular tubes, especially those with a rectangular, annular or oval cross section, but then other functional relationships which deviate from equation (2) must be specified. For multi phase fluids a relationship between effective viscosity and the pressure drop which is represented as more complex than equation (2) can also be used.

Therefore, to determine dynamic viscosity $\eta$, in addition to the geometrical data, V and $\Delta p$ must be known For burner control, the volumetric flow should be low in order on the one hand to keep the space requirement for the device low by using small capillaries and on the other hand to keep down the inlet effects of the flow, which become more significant at large volumetric flows and which can lead to larger measurement errors. Moreover, low costs result from the use of small capillaries. The measurement of very small volumetric flows is very difficult. Therefore a constant, very low volumetric flow should be made available as much as possible. This can happen especially according to one embodiment of the invention by means of a micro pump, especially a semiconductor micro pump. The pressure loss can be measured in the conventional manner (piezoelectrically). Moreover, for determining the dynamic viscosity $\pi$, the relationship between temperature and dynamic viscosity can be considered. The manner of operation of an equipped viscosity sensor which is advantageously used in the invention can be described as follows:

The pump delivers a constant, known volumetric flow through the capillary via which the pressure drop is measured. With consideration of the gas temperature, an electronic signal is then determined which corresponds to the viscosity and thus also to the Wobbe index or to other fuel quality values, especially the minimum air demand, heating output and calorific value. As alternatives, measurement of V and $\Delta p$ or controlled adjustment of $\Delta p$ and measurement of V can also be done. Measurement or stipulation of a special pressure signal can even be abandoned if the power losses of the metering pumps are low in the future such that the pressure loss can be determined via the power consumption of the pump. The invention uses the theoretical consideration that, when the gas composition changes, the following applies:

$$\lambda_2 = \lambda_1(\rho_2/\rho_1)^{0.5}(L_{min\,1}/L_{min\,2}) \approx \lambda_1(W_{0,1}/W_{0,2}) \approx \lambda_1(W_{u,1}/W_{u,2}) \quad (3)$$

if the volumetric flow of the fuel due to turbulent choking would behave in inverse proportion to the square root of the specific gravity of the fuel. The air ratio $\lambda_2$ generally changes somewhat proportionally to the ratio of the Wobbe index ($W_O$=upper Wobbe index; $W_u$=lower Wobbe index) and the primary air ratio in nominal operation $\lambda_1$. Here $\rho_{1,2}$ combustible gas density and
$L_{min\,1,2}$ minimum air requirement Conversely, if no turbulent choking takes place, but laminar through-flow at constant $\Delta p$ occurs, the following applies:

$$\lambda_2 = \lambda_1(\mu_2/\mu_1)(L_{min,1}/L_{min,2}) \quad (4)$$

If a process is used in which the volumetric flow of the combustible gas were to behave independently of the combustible gas density, the following simple relationship applies:

$$\lambda_2 = \lambda_1(L_{min,1}/L_{min,2}) \quad (5)$$

The aforementioned computations show that in the ideal case, for determining viscosity, it is sufficient to determine the calorific value and the necessary amount of air. In any case, the conditions which prevail in practice deviate in principle from the idealized conditions examined above so that generally a simple relationship is not expected, and the measured characteristic should be relied upon.

This determination of the calorific value and thus of the Wobbe index can, however, be further improved according to one advantageous feature of the invention in which there is at least one measurement point for detecting the temperature at least of a partial amount of the oxidation agent/fuel mixture. Based on the temperature measurement, the viscosity and thus the Wobbe index can be detected much better. The measured temperature can, however, also be introduced as an additional parameter in order to better determine the Wobbe index or the calorific value and thus the required air via a family of characteristics.

The measurement accuracy is increased mainly according to one advantageous feature of the invention in which the measurement device detects solely the viscosity of the fuel or a function of the viscosity.

If on the other hand the viscosity of the air/fuel mixture were determined, then for example the parameters of the added air would have to be used for adjustment. This would unnecessarily complicate the device. For this reason, as already stated above, open-loop control is more favorable than closed-loop control by means of the device.

In addition to other known devices for determining the viscosity, the measurement device, as provided according to one preferred embodiment of the invention, is a tube viscosimeter with which the dynamic viscosity can be determined via the relationship between the pressure drop over the tube, the volumetric flow and optionally also the temperature. In particular, one such measurement device has the advantage of being especially simple and having a less complex viscosity determination.

In another preferred embodiment of the invention it is provided that the dimensions of the tube are chosen such that the flow is essentially laminar or is at least in the transition range between the turbulent and laminar flow.

In this embodiment, the flow is limited to being essentially laminar. This has the advantage of very simple determination of closed-loop control according to the equations given above. Conversely, in essentially turbulent flows it would be recommended that for each device for better determination of the viscosity its own family of characteristics be determined. This would increase the production process and the cost for production of the device as claimed in the invention.

Fundamentally, under these conditions any tube can be used, whether straight or curved or bent into any shape. In principle any cross section is possible. In particular, the cost is especially reduced according to two preferred features of the invention, namely: (1) the tube is straight; and (2) the tube has a uniform, especially circular cross section over its length.

In this respect fundamentally any tube diameter can be chosen. But it is advantageous above all if only little gas is used for measurement and the pressure rise becomes as high as possible for viscosity determination, therefore a transition essentially to a capillary takes place. This is considered in one preferred feature of the invention in which it is provided that the tube diameter is less than 0.2 mm. This dimensioning means above all, and in combination with the above discussed features of the invention, especially good detection of the viscosity via the pressure drop or flow velocity.

Using a viscosimeter, specifically the viscosity can be determined especially by measuring the pressure loss after flow through the tube or also by the flow velocity at a constant pressure difference. Furthermore, it is possible to use any combination of flow conditions and the pressure drop via the known flow equations for determining the viscosity.

But, in particular, according to one feature of the invention it is preferred that the pressure drop over the tube or at least within a partial tube piece can be detected by measurement technology, with the flow velocity then being kept essentially constant.

Pressure changes at the input of the tube can slightly adulterate the measurement. In order to counteract these disruptive effects at the tube input, it is provided according to one advantageous development that the tube inlet is rounded.

In particular, with respect to establishing the tube dimensions, dimensioning has become especially advantageous with respect to a Reynolds number less than 1000.

It is especially simple in terms of measurement engineering if there is a controllable pump for adjusting the volumetric flow in the tube. When the volumetric flow is kept constant, the viscosity can be determined easily via pressure measurement and for optionally highly variable temperatures also by consideration of the temperature via an additional temperature measurement. This can be easily done chiefly when the pump is controlled such that the volumetric flow is controlled to be constant especially via this controllable pump according to one preferred development of the invention.

Another possibility however for the controllable pump is that the pump is regulated with respect to a constant pressure drop over the tube. Then the viscosity is determined essentially via the volumetric flow which then can be determined solely via pump control. For the corresponding required measurement accuracy the measured value can also be improved via an additionally measured temperature. Pumps can be especially metering pumps, rotating or oscillating positive-displacement pumps, and rotating or oscillating displacement compressors. According to one preferred development of the invention it is however provided that the pump is a micro pump. These pumps are micro mechanical components which are economical and simple in structure. In particular, they are also tolerant of bubbles due to the small quantities which are delivered. One such pump is described for example in the article "A self-priming and bubble-tolerant piezoelectric silicon micro pump for liquids and gases", Micro Electro Mechanical Systems MEMS. Jan. 25–29, 1999, Germany, by R. Lineman et al.

The device according to two developments of the invention becomes especially compact and less complex; in it the semiconductor micro pump and at least parts of the circuit (28), especially also the pressure and temperature sensor, are integrated on a common substrate and/or the pressure drop over the tube can be determined via the power consumption of the pump.

In particular, in the last development of the invention a pressure sensor can be saved by using the power consumption of the pump as a measure for the pressure.

Power losses of the pumps, especially micro pumps, can currently by reproduced such that the power can be easily calibrated via a calibration curve into pressure or even the desired viscosity.

In another preferred development of the invention there is a burner control by which adjustment of the oxidation agent/fuel mixture is active before ignition and by which optionally the composition of the oxidation agent/fuel mixture can be continuously controlled during combustion. Thus, the detailed advantages of continuous burner operation and especially also low-pollution ignition are easily accomplished.

Under especially constant conditions, for example, at guarantee values for fluctuations of the Wobbe index by the gas suppliers, it is sufficient if the burner control is active before and/or during the ignition process. Further control in continuous operation can then be omitted.

On the other hand, it is recommended especially for very highly fluctuating gas supplies to operate the control even after ignition, continually or at uniform measurement intervals. Continuous operation should be preferred in this case.

It is especially advantageous, if the device is miniaturized, to design it as part of the gas unit used for the burner. This advantage arises especially when the device, as indicated above, is made as an integrated solid state component.

The measured fuel or the measured fuel mixture can of course also be dissipated into the environment in the simplest case. But this would pollute the environment unnecessarily, even if micro pumps with only small volumetric flows are used.

To minimize this environmental burden, the invention is preferably developed by there being a means, especially the fan of the burner, for returning the partial mixture to the feeding pipe of the burner which allows the initial pressure of the measured partial mixture to be uninfluenced.

As becomes apparent, in particular the fan is especially suited for this purpose. In this way it is simply enabled that the initial pressure of the partial mixture remains largely unchanged, so that inaccuracies in measurement engineering can also be easily avoided.

In one preferred development it is provided that a reference gas can be supplied to the measurement device. The viscosity sensor can be calibrated using this reference gas.

Other advantages and features of the invention will be better understood by reference to the following embodiments represented in the accompanying drawings, wherein.

One important physical concept for the relationships of interest here is the upper Wobbe index which is defined as the heat output through by the square root of the ratio of the specific gravity of the gas to the specific gravity of the air under normal conditions. As was shown in FIG. 1, there is an empirical, functional relationship between this Wobbe index and the dynamic viscosity.

Figure 1:
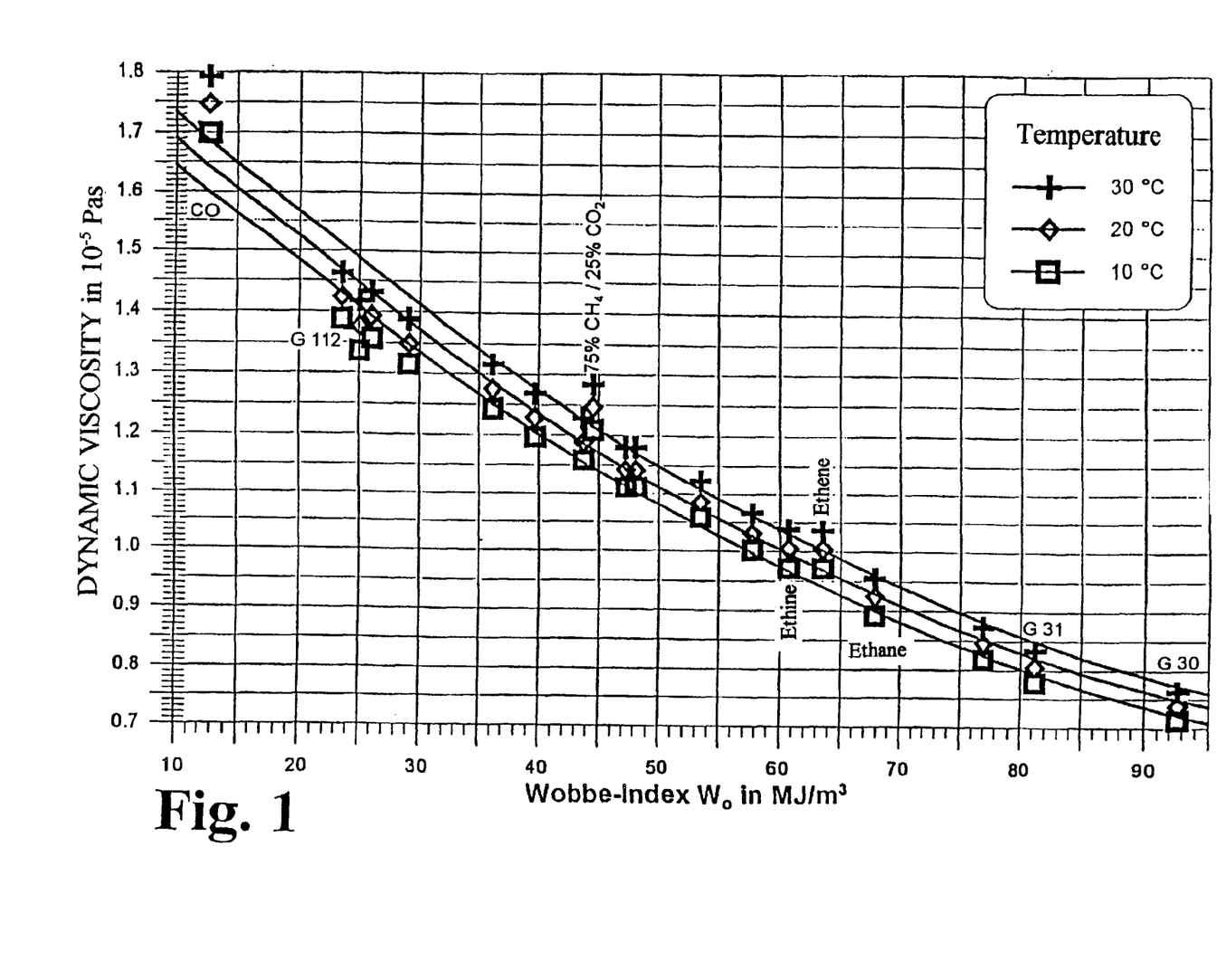
FIGS. 1 to 3 are different diagrams showing the relationship between the dynamic viscosity and various combustible gas properties which characterize the combustion behavior.

The relationship between the dynamic viscosity and the Wobbe index is shown in FIG. 1, in which for various fuels individual measurement points for these two quantities are entered. Some fuels are labeled with the designation which is accepted in the sector for heating technology of the European Community.

Accordingly, there is a simple functional relationship between the dynamic viscosity and the Wobbe index which is shown by the solid lines, and which is essentially maintained in the range of ±10% for different fuels.

FIG. 1 plots mainly data for different temperatures of the fuel at 10° C., 20° C. and 30° C. It is also shown here that the functional relationship between the Wobbe index and viscosity within moderate tolerances is essentially independent of the temperature. Good determination of viscosity with simultaneous consideration of the temperature can however greatly improve control of the burner with respect to the calorific values supplied to it via dynamic viscosity.

Figure 2:
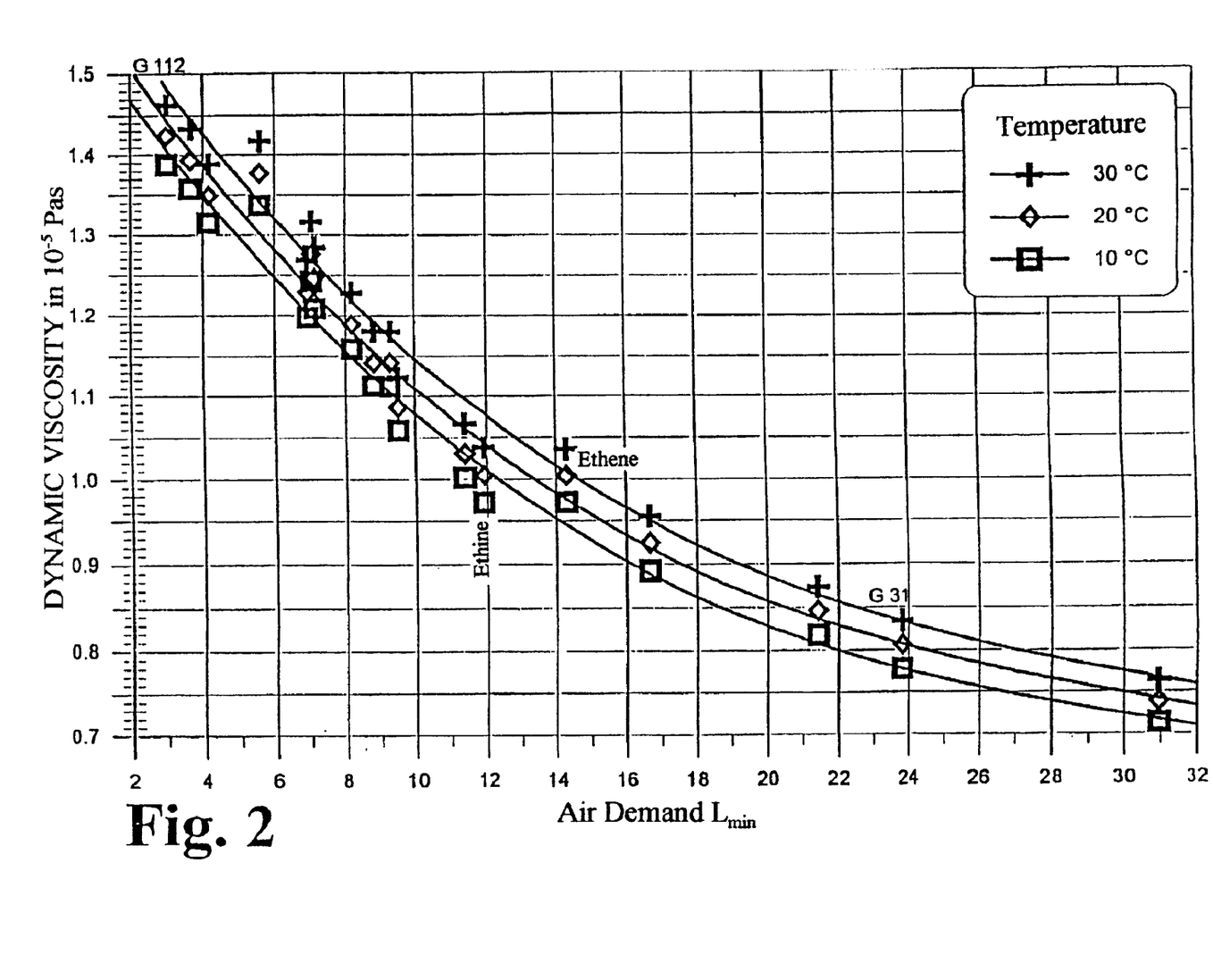
Figure 3:
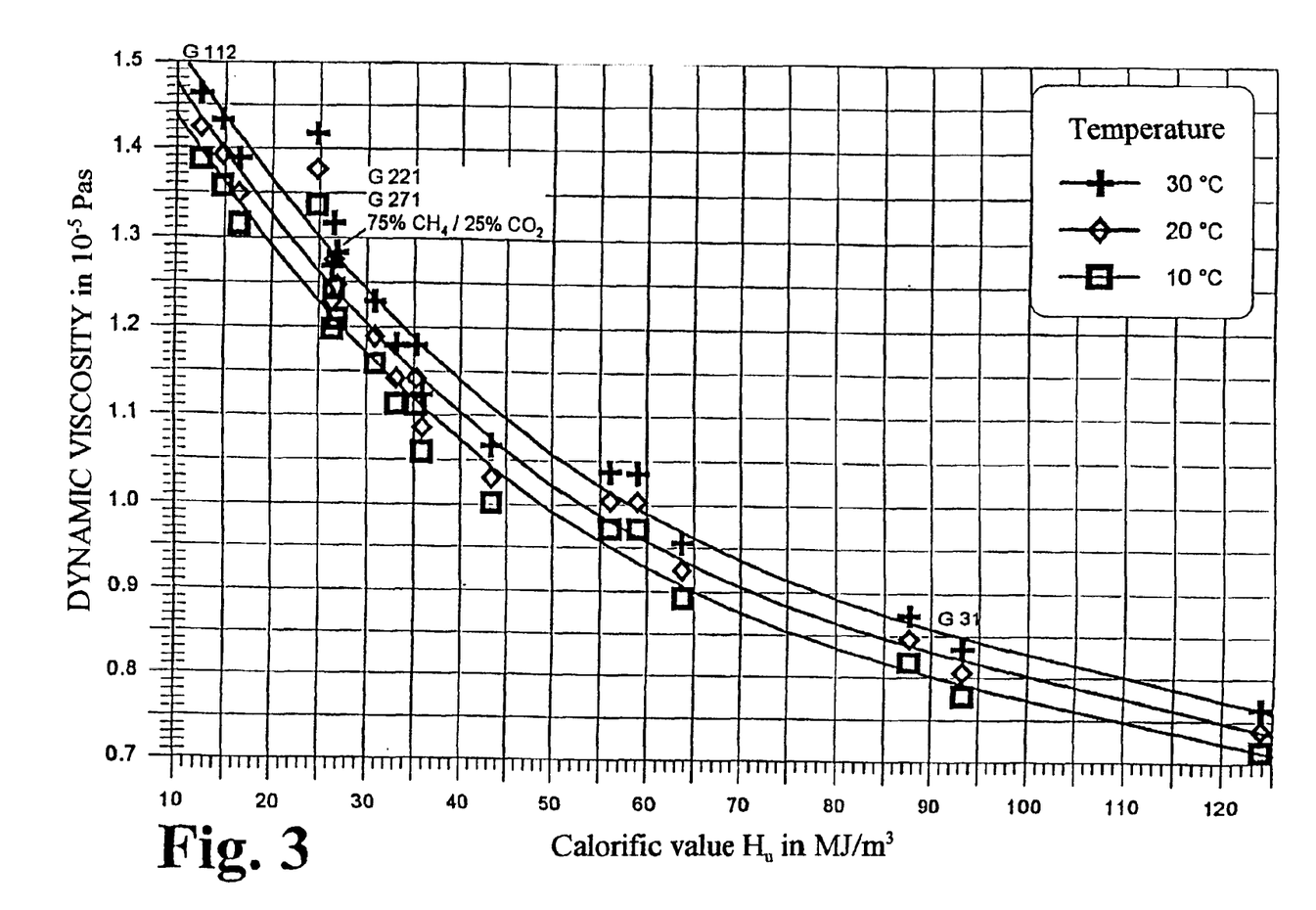

As the calorific value increases, the oxidation agent demand for complete combustion which can be supplied for example from the ambient air also increases. Based on the illustrated relationships, it should also be possible to control the air demand via measurement of the dynamic viscosity. As is apparent from FIG. 2, in which for various fuels the dynamic viscosity in pascal seconds is plotted versus air demand, accordingly there is likewise a simple relationship between the air demand and the dynamic viscosity with only minor deviations. FIG. 2 shows that the suitable air demand can be optimally set within limits of 10% based on the measured dynamic viscosity. In particular, there is also a similar relationship between the calorific value of the current fuel and the viscosity, as can be seen in FIG. 3.

These three figures make it clear that control of the combustible gas composition of the most varied types with respect to the supplied oxidation agent or air is ideally suited for optimum burner operation.

Figure 4:
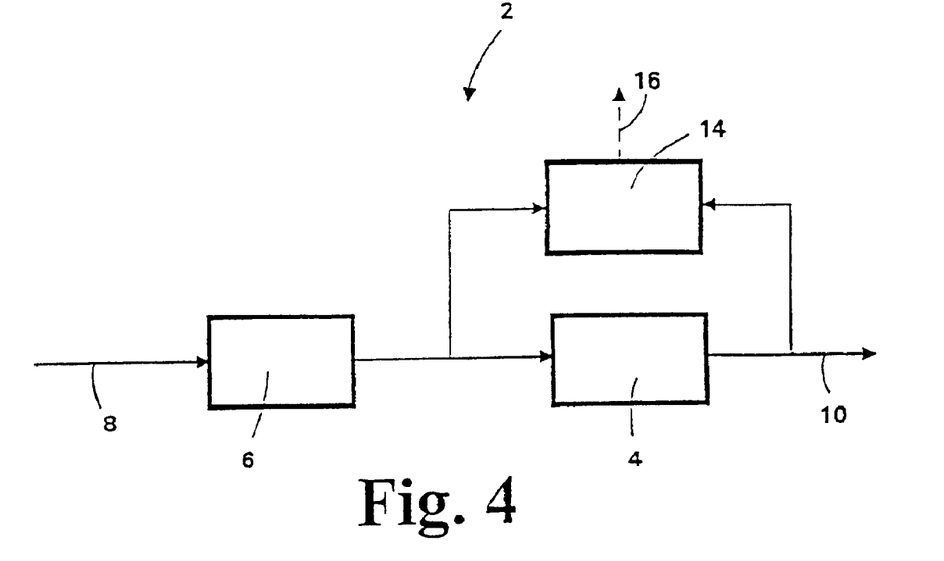
FIG. 4 is a diagram showing possible structure for a measurement device for determining the viscosity.

One especially preferred embodiment for a viscosity sensor 2 as the measurement device for viscosity is shown in FIG. 4. One such sensor is also known as a tube viscosimeter. When this viscosity sensor 2 was designed, attention was focused mainly on using only little fuel for measurement. For this reason, a capillary to which the fuel is supplied with a micro pump 6 was used as the tube.

The fuel was supplied through the tube 8, the outlet via the tube 10.

Figure 5:
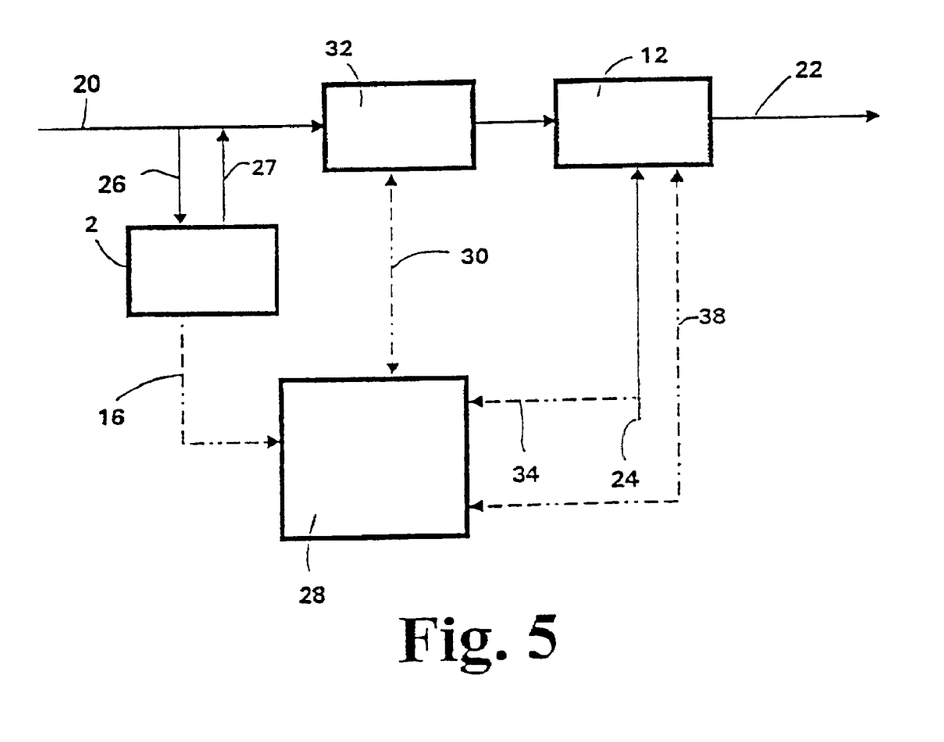
FIG. 5 is a diagram showing an embodiment for use of a measurement device as shown in FIG. 4 in the overall burner control combination.
Figure 6:
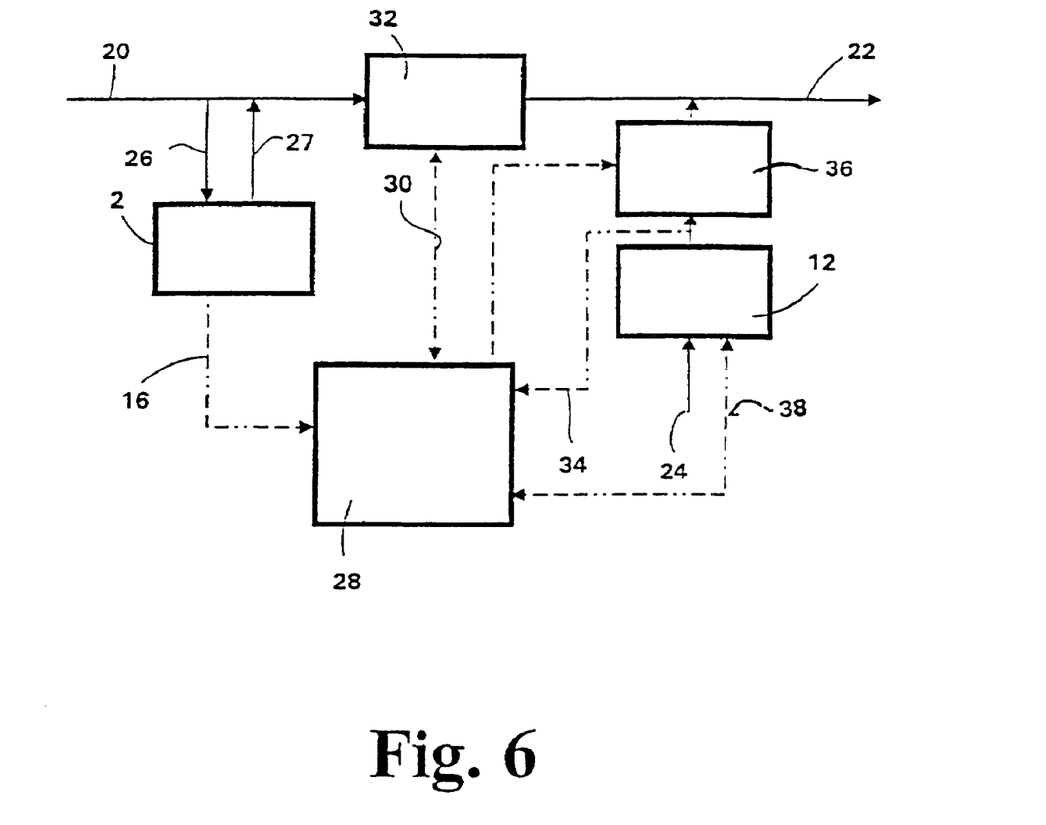
FIG. 6 is a diagram showing another embodiment for use of a measurement device as shown in FIG. 4 in the overall burner control combination.

Due to the required small amounts, the fuel could easily be allowed to escape into the air. But as can be seen in FIGS. 5 and 6, it can also be delivered again to the fuel.

The micro pump 6 in the embodiment of FIG. 4 was triggered for a constant volumetric flow. The volumetric flow was chosen such that on the inserted capillary 4 a suitably large pressure increase takes place in order to be able to determine the viscosity with sufficient accuracy. There is a pressure sensor 14 for determining the differential pressure at the outlet and the inlet of the capillary 4. The pressure sensor 14 is furthermore equipped with a temperature sensor so that the two, specifically the pressure drop and also the temperature of the gas, are available for more accurate determination of viscosity.

The electrical signals produced by the pressure and temperature sensor 14 were supplied to evaluation electronics via a line 16. The evaluation electronics consisted essentially of two analog/digital converters with which the signals for the pressure difference and the temperature were converted into digital values. The evaluation electronics furthermore contains a processor unit with which the digital values could be read in and which computed a data value for the viscosity from the converted values. In particular a program run was provided for the processor which converts the data value which was determined in this way for the viscosity using the characteristic into a control quantity for adding air or fuel to produce the suitable oxidation agent/fuel mixture.

The characteristic used for this purpose is formed especially easily when the flow through the capillary 4 lies essentially in the laminar range. The flow could also be between laminar and turbulent in the transition range, but operation in the area of turbulent flow should be recommended less due to the resulting inaccuracy caused by separation of vortices and the like.

Therefore the capillary 4 was designed for a Reynolds number less than 1000. In particular, tube diameters below two millimeters and especially below 0.2 millimeter are suitable for practical embodiments.

In particular, in the embodiment in FIG. 4 it happens that both the micro pump as a micro mechanical component and also the capillary, the pressure and temperature sensors can be implemented on a single substrate. Since these components can be produced with processes which are conventional in semiconductor engineering, it is also possible to integrate even the evaluation electronics with analog/digital converters and the processor on the same substrate so that overall an especially small component results which can be used essentially in any burner control.

How this temperature sensor 2 can be integrated in a burner control is explained in particular especially in the embodiments from FIGS. 4 and 5.

FIGS. 5 and 6 differ essentially in that in FIG. 5 the fuel supply is regulated, in FIG. 6 conversely, the air supply.

For the sake of simplification, the structural components for practical implementation of the embodiment have been omitted. In the corresponding laboratory set up it was provided for example that the lines 8 and 10 could be decoupled from the burner control by means of valves, and a reference gas, for example the ambient air, was routed through the viscosity sensor for calibration. Thus, mechanical tolerances, changes in the pressure sensor, the pump and the like can also be considered so that even over longer time intervals proper operation of the burner control is easily possible.

In both embodiments from FIG. 5 and FIG. 6 the fuel is delivered via a feed line 20 and the oxidation agent/fuel mixture which has been suitably mixed via the viscosity is supplied to a burner via a feeding pipe 22.

The oxidation agent needed for combustion is supplied as a portion of the ambient air which enters via an inlet 24 into the devices shown. It is common to both examples that the fuel is supplied from the feed line 20 via a line 26 into the viscosity sensor 2 described above and the measured amount of fuel is then supplied again to the overall fuel flow via the line 27. The feed point is actually not critical for operation. But it was ascertained that measurement and adjustment are especially noncritical when the line 27 is not returned to the fuel line 20, as is shown in the examples from FIG. 5 and FIG. 6, but to a fan 12 which is intended for air feed.

The measured values for the gas temperature, the pressure and the volumetric flow are supplied via feed lines 16 to a control means 28 which is used not only for implementation of the additional functions by detection of the type of gas, but also performs all the tasks of a conventional burner control. Using a line 30 electrical signals are transferred to a gas unit 32 with which the fuel supply is controlled in the conventional manner. Furthermore, the electrical gas unit also transfers data, especially manual settings for summer and winter operation, via the line 30 to the control means 28. The gas unit 32 can be made both electrical and also pneumatic. In the case of a pneumatic combination an additional actuator is necessary.

Furthermore, another line 34 in the control means 28 which can be used for example for an additional function is shown as in FIGS. 5 and 6. In the embodiments, a signal for the air temperature is transmitted with this line 34 in order to enable still better adjustment of the oxidation agent/fuel mixture. Of course also other physical values of the ambient air can be measured and used for adjustment. For example, with one such control means also air pressure or atmospheric humidity can be taken into account when they are supplied in the form of suitable signals via other families of characteristics.

As can be seen from FIG. 5, the amount of fuel in this example is regulated by the gas unit 32 and when the performance of the burner is adjusted, air is added almost constantly via the fan 12 before the oxidation agent/fuel mixture which has been formed in this way is routed into the feeding pipe 22 for the burner. Conversely, in FIG. 6, behind the fan 12 for feeding air there is an actuator 36 with which the amount of air is regulated. In addition, the fan 12 is also controlled for determining the delivery amount by the control means 28 via the control line 38.

The examples shown above are exemplary. Initially several modification possibilities were indicated. It is especially possible to keep the pressure on the viscosity sensor 2 constant by triggering the micro pump 6 with respect to a constant pressure difference via the capillary 4. The controlled variable for adjusting the micro pump 6, especially the pump frequency, is then directly a measure for the volumetric flow. Thus the volumetric flow, temperature and pressure can be used for control.

In particular it has been shown that for very simple burners, if the control accuracy does not meet the highest requirements, special temperature measurement is not necessary. In addition to the mixing proportions, air and fuel, which are controlled in the example in FIG. 5 and FIG. 6, other gases can also be added to control the burner according to the calorific value of the supplied fuel. But it is common to all these modification possibilities that the viscosity is determined via a viscosity sensor 2 as accurately as is necessary for the respective application. A signal for dynamic viscosity or a complex function of it is used in order to control the oxidation agent/fuel mixture in the feeding pipe 22 for a burner for optimum heating or also low emissions.

The process suggested here works completely independently of the burner condition. In this way, in the ignition phase it can also be used for the burner so that in this phase pollutant emission as low as possible can be accomplished and the ignition process is facilitated.

Another possibility of use consists in operating the burner in a modulating manner, opposite control via the mode of operation necessary for ionization flow measurements. This is associated with technical difficulties especially for control of the oxidation agent/fuel mixture composition by means of ionization flow measurement, since the reference ionization flow also changes with the change in performance.

This continuous operation greatly reduces the heating costs. But in particular there is the advantage that based on the more complete combustion compared with many conventional burners the maintenance intervals are lengthened, because the burner need only be operated very briefly at highest power.

In particular, it should be emphasized that exhaust emissions are much less as a result of the optimum oxidation agent/fuel mixture composition and that especially for low-caloric gases due to optimum oxidation agent/fuel mixture composition a higher combustion efficiency is achieved overall so that heating costs are also reduced.

What is claimed is:

1. A device for adjusting the oxidation agent/fuel mixture in the feeding pipe of a burner, said device comprising:

means for changing the composition of the oxidation agent/fuel mixture in the feeding pipe;

a measurement device for detecting the condition of one of the fuel or oxidation agent/fuel mixture;

a circuit for controlling the means for changing the composition depending on the condition which has been detected by the measurement device; and a controllable pump for adjusting the volumetric flow in the tube; wherein the measurement device is a tube viscosimeter with which the dynamic viscosity can be determined via a relationship between the pressure drop over the tube and the volumetric flow; and said measurement device detects the calorific value or the Wobbe index of at least a portion of the fuel or oxidation agent/fuel mixture by measuring the viscosity of said portion or a function of it before combustion; said measurement device being located upstream, in terms of the direction of flow, of said means for changing the composition, and said circuit provides open-loop control of said means for changing the composition of the oxidation agent/fuel mixture according to the detected viscosity, or said measurement device being located downstream, in terms of the direction of flow, of said means for changing the composition, and said circuit provides closed-loop control of said means for changing the composition of the oxidation agent/fuel mixture.

2. The device as claimed in claim 1, wherein the pressure drop over the tube is regulated by adjusting the controllable pump.

3. The device as claimed in claim 1, wherein the controllable pump is a semiconductor micro pump.

4. The device as claimed in claim 3, wherein the semiconductor micro pump, a pressure sensor and a temperature sensor are integrated on a common substrate.

5. The device as claimed in claim 1, wherein the pressure drop over the tube is determined using the power consumption of the controllable pump.

6. The device as claimed in claim 1, wherein the controllable pump controls the volumetric flow rate so as to be substantially constant.

* * * * *

UNITED STATES PATENT AND TRADEMARK OFFICE
CERTIFICATE OF CORRECTION

PATENT NO. : 6,872,071 B1
APPLICATION NO. : 09/959436
DATED : March 29, 2005
INVENTOR(S) : Durst

It is certified that error appears in the above-identified patent and that said Letters Patent is hereby corrected as shown below:

Column 5
Line 3, change the exponent in equation (1) from "05" to -- 0.5 -- ;
Line 37, change "known For" to -- known. For--; and Column 6
Line 4, change the exponent in equation (3) from "05" to -- 0.5 -- .

Signed and Sealed this

Sixth Day of March, 2007

JON W. DUDAS
*Director of the United States Patent and Trademark Office*